United States Patent
Ma et al.

(10) Patent No.: US 10,564,079 B2
(45) Date of Patent: Feb. 18, 2020

(54) DEVICE, SYSTEM AND METHOD FOR TRIAXIAL COMPRESSION TEST WITH/WITHOUT JACKET BY GAS CONFINING PRESSURE ON ROCK

(71) Applicant: INSTITUTE OF ROCK AND SOIL MECHANICS, CHINESE ACADEMY OF SCIENCES, Wuhan (CN)

(72) Inventors: Hongling Ma, Wuhan (CN); Xilin Shi, Wuhan (CN); Yuhao Zhang, Wuhan (CN); Yintong Guo, Wuhan (CN); Chunhe Yang, Wuhan (CN); Yinping Li, Wuhan (CN); Tongtao Wang, Wuhan (CN); Yue Han, Wuhan (CN); Hongwu Yin, Wuhan (CN)

(73) Assignee: INSTITUTE OF ROCK AND SOIL MECHANICS, CHINESE ACADEMY OF SCIENCES, Wuhan (CN)

( * ) Notice: Subject to any disclaimer, the term of this patent is extended or adjusted under 35 U.S.C. 154(b) by 34 days.

(21) Appl. No.: 16/028,584

(22) Filed: Jul. 6, 2018

(65) Prior Publication Data
US 2019/0265138 A1    Aug. 29, 2019

(30) Foreign Application Priority Data
Feb. 27, 2018    (CN) .......................... 2018 1 0162388

(51) Int. Cl.
*G01N 3/10*    (2006.01)
*G01N 33/24*    (2006.01)

(52) U.S. Cl.
CPC ............... *G01N 3/10* (2013.01); *G01N 33/24* (2013.01); *G01N 2203/0019* (2013.01); *G01N 2203/0256* (2013.01)

(58) Field of Classification Search
CPC .. G01N 3/10; G01N 3/12; G01N 3/02; G01N 2203/0256
See application file for complete search history.

(56) References Cited

U.S. PATENT DOCUMENTS 4,009,977 A * 3/1977 Chao ..................... B30B 11/001
                                                         425/78
4,615,221 A * 10/1986 Mellor ..................... G01N 3/10
                                                          73/778

(Continued)

FOREIGN PATENT DOCUMENTS

CN    103344496 B  *  9/2015
CN    105181469 A  *  12/2015

(Continued)

*Primary Examiner* — Jonathan M Dunlap
(74) *Attorney, Agent, or Firm* — Platinum Intellectual Property LLP

(57) ABSTRACT

The present invention discloses a device, system and method triaxial compression test with/without jacket by gas confining pressure on rock, and belongs to the technical field of rock mechanics tests. The device includes a container, wherein an accommodating cavity is disposed in the container for placing a core sample, a first through hole and a second through hole are respectively disposed at an upper end of the container, the first through hole is used for penetration of an end cap for loading an axial pressure to the core sample, the second through hole is used for injecting a gas into the accommodating cavity so as to apply a gas confining pressure on the core sample, a third through hole is disposed at a lower end of a side wall of the container, and the third through hole is used for communicating the accommodating cavity with the triaxial cell so as to achieve pressure transfer and balance between the accommodating cavity and the triaxial cell. During application, the device is installed in the triaxial cell. The container is inflated by a gas inlet and outlet of the triaxial cell and a communicating tube, (Continued)

the internal pressure applied by a high pressure gas on a near field rock wall of a salt cave can be accurately simulated, and a triaxial compression test with/without jacket by gas confining pressure on rock is conducted.

8 Claims, 9 Drawing Sheets

(56) References Cited

U.S. PATENT DOCUMENTS

| | | | | |
|---|---|---|---|---|
| 5,226,310 | A * | 7/1993 | Steiger | E21B 49/006 |
| | | | | 73/38 |
| 6,591,690 | B1 * | 7/2003 | Crockford | G01N 3/10 |
| | | | | 73/760 |
| 7,143,653 | B2 * | 12/2006 | Abdel-Hadi | G01N 3/10 |
| | | | | 73/819 |
| 7,472,588 | B2 * | 1/2009 | Slavin | G01N 15/08 |
| | | | | 324/376 |
| 8,561,474 | B2 * | 10/2013 | Secq | E21B 21/08 |
| | | | | 73/825 |
| 8,770,038 | B2 * | 7/2014 | Secq | E21B 21/08 |
| | | | | 73/783 |
| 8,783,091 | B2 * | 7/2014 | Meadows | G01N 3/08 |
| | | | | 73/37 |
| 9,594,009 | B2 * | 3/2017 | Meadows | G01N 3/08 |
| 2004/0194543 | A1 * | 10/2004 | Abdel-Hadi | G01N 3/08 |
| | | | | 73/149 |
| 2008/0257030 | A1 * | 10/2008 | Slavin | G01N 15/08 |
| | | | | 73/152.11 |
| 2011/0094295 | A1 * | 4/2011 | Meadows | G01N 3/08 |
| | | | | 73/38 |
| 2011/0107844 | A1 * | 5/2011 | Secq | E21B 21/08 |
| | | | | 73/825 |
| 2011/0132099 | A1 * | 6/2011 | Secq | E21B 21/08 |
| | | | | 73/821 |
| 2014/0137660 | A1 * | 5/2014 | Meadows | G01N 3/08 |
| | | | | 73/818 |
| 2017/0150015 | A1 * | 5/2017 | Salazar | H04N 5/2252 |
| 2019/0025169 | A1 * | 1/2019 | Zhang | F17C 13/002 |

FOREIGN PATENT DOCUMENTS

| | | |
|---|---|---|
| KR | 101683619 B1 * | 12/2016 |
| SU | 1264041 A1 * | 10/1986 |

* cited by examiner

DEVICE, SYSTEM AND METHOD FOR TRIAXIAL COMPRESSION TEST WITH/WITHOUT JACKET BY GAS CONFINING PRESSURE ON ROCK

CROSS-REFERENCES TO RELATED APPLICATIONS

This application is a Non-provisional Application under 35 USC 111(a), which claims priority of Chinese Patent Application Serial No. 201810162388.3, filed Feb. 27, 2018, the disclosure of which is hereby incorporated by reference in their entirety.

TECHNICAL FIELD

The present disclosure relates to the technical field of rock mechanics test, and particularly to a device, system and method for triaxial compression test with/without jacket by gas confining pressure on rock.

BACKGROUND OF THE INVENTION

Actually, no matter salt caverns used for gas storage or compressed air energy storage, underground salt caverns are all filled with high-pressure gases. Under the high-pressure of gas, surrounding rock of the salt caverns may be deformed, greatly impacting the engineering stability of the salt caverns which used for gas storage or compressed air energy storage. Therefore, it is particularly important to test the deformation and strength characteristics of salt rock under the high-pressure gases. However, in the prior art, there is no test equipment for this case and a triaxial compression test with/without jacket by gas confining pressure on rock gases cannot be conducted.

SUMMARY OF THE INVENTION

In view of this, the present disclosure provides a device, system and method for triaxial compression test with/without jacket by gas confining pressure on rock. The triaxial compression test with/without jacket by gas confining pressure on rock can be conducted, and an internal pressure applied by a high-pressure gas on the near-filed surrounding rock of salt caverns can be accurately simulated.

In order to achieve the above objective, the present disclosure adopts the following technical solutions:

On a first aspect, the present disclosure provides a device for triaxial compression test with/without jacket by gas confining pressure on rock, applied for a system for triaxial compression test with/without jacket by gas confining pressure on rock. The system further includes a triaxial cell. The device includes a container, and wherein an accommodating cavity is disposed within the container for placing a core sample. A first through hole and a second through hole are respectively disposed at an upper end of the container, the first through hole is for an end cap for loading an axial pressure to the core sample to penetrate through, and the second through hole is used for injecting gas into the accommodating cavity so as to apply a confining pressure on the core sample by high-pressure gas entering into the accommodating cavity. A third through hole is disposed at a lower end of a side wall of the container and used for communicating the accommodating cavity with the triaxial cell.

Further, the device for triaxial compression test with/without jacket by gas confining pressure on rock further comprising a communicating tube, wherein one end of the communicating tube is in sealed fit with the second through hole and in communication with the accommodating cavity, and the other end of the communicating tube is used for connecting a gas inlet and outlet provided on the triaxial cell.

Further, the device for triaxial compression test with/without jacket by gas confining pressure on rock further comprising a first rubber stopper with a hole, and one end of the communicating tube is in sealed fit with the second through hole through the first rubber stopper with a hole.

Further, the communicating tube comprising a first connecting tube and a second connecting tube. One end of the first connecting tube is in sealed fit with the second through hole, and the other end of the first connecting tube is connected with one end of the second connecting tube. The other end of the second connecting tube is used for connecting the gas inlet and outlet provided on the triaxial cell.

Further, the first connecting tube is a U-shaped tube, one end of the U-shaped tube is in sealed fit with the second through hole, and the other end of the U-shaped tube stretches out from an outer edge of a cover plate of the container.

Further, the second connecting tube is a rubber tube.

Further, the device for triaxial compression test with/without jacket by gas confining pressure on rock further comprising an upper end cap, wherein one end of the upper end cap is used for connecting a top end of the core sample, and the other end of the upper end cap penetrates through the first through hole to serve as an axial pressure bearing surface.

Further, the device for triaxial compression test with/without jacket by gas confining pressure on rock further comprising a lower end cap, wherein one end of the lower end cap is used for connecting a lower platen of the container, and the other end of the lower end cap is used for connecting a bottom end of the core sample.

Further, the cover plate, the lower platen and the side wall of the container are separate, the side wall is cylindrical, and the cover plate and the lower platen are separately in sealed fit with the side wall. The first through hole and the second through hole are respectively disposed at the cover plate, and the third through hole is disposed at the bottom of the side wall.

Further, the device for triaxial compression test with/without jacket by gas confining pressure on rock further includes a first annular sealing element and a second annular sealing element, one end of the side wall is in sealed fit with the cover plate through the first annular sealing element, and the other end of the side wall is in sealed fit with the lower platen through the second annular sealing element.

On a second aspect, the present disclosure further provides system for triaxial compression test with/without jacket by gas confining pressure on rock including a triaxial cell and the device for triaxial compression test with/without jacket by gas confining pressure on rock mentioned above. The device is installed within the triaxial cell. A gas inlet and outlet is provided on a lower platen of the triaxial cell, the gas inlet and outlet is used for connecting an external air inflation and pressurization device, and the gas inlet and outlet is in communication with the second through hole of the device through a communicating tube.

Further, an outer end of the gas inlet and outlet is provided with an intake tube stretching out of the triaxial cell, and a gas port valve for controlling the connection and disconnection of the intake tube is provided on the intake tube.

Further, an inner end of the gas inlet and outlet is provided with a second rubber stopper with a hole, and an outer wall of the second rubber stopper with a hole is in sealed fit with an inner wall of the gas inlet and outlet, a conduit in sealed fit with the hole is disposed in the hole of the second rubber stopper with a hole, and the communicating tube communicates with the gas inlet and outlet through the conduit.

Further, the system for triaxial compression test with/without jacket by gas confining pressure on rock further includes an external liquid storage device and a liquid delivery tube, the external liquid storage device is used for storing hydraulic oil, one end of the liquid delivery tube is in communication with a first oil port of the upper end of the triaxial cell, and the other end of the liquid delivery tube is immersed into the hydraulic oil within the external liquid storage device.

Further, the air inflation and pressurization device is a high pressure gas cylinder.

On a third aspect, the present disclosure further provides a method to conduct the triaxial compression test with/without jacket by gas confining pressure on rock, implemented on the basis of the device for triaxial compression test with/without jacket by gas confining pressure on rock mentioned above. The method includes: mounting a core sample in a container of the device; mounting the device in a triaxial cell, and causing an end cap to pass through a first through hole of the device until contacting a top of the core sample, wherein the end cap is used for loading an axial pressure to the core sample; injecting hydraulic oil into a space between the triaxial cell and the container through the first oil port of the lower platen of the triaxial cell; connecting the gas inlet and outlet of the triaxial cell with the air inflation and pressurization device, inflating the container through the air inflation and pressurization device, the gas inlet and outlet, the communicating tube and the second through hole of the device so as to apply a confining pressure with a preset magnitude on the core sample; loading the axial pressure to the core sample according to a preset rule; releasing a high pressure gas within the device, and discharging the hydraulic oil in the triaxial cell, after the test ends.

Further, a lower end cap is installed within the container of the device for triaxial compression test with/without jacket by gas confining pressure on rock mentioned above, the core sample is installed on the lower end cap, one end of the lower end cap is connected with the lower platen of the container, and the other end of the lower end cap is connected with the bottom end of the core sample. At this time, between the step of injecting hydraulic oil into the space between the triaxial cell and the container through the first oil port of the lower platen of the triaxial cell and the step of connecting the gas inlet and outlet of the triaxial cell with the air inflation and pressurization device, the method for triaxial compression test with/without jacket by gas confining pressure on rock further includes: connecting a second oil port of the upper end of the triaxial cell to an external liquid storage device holding the hydraulic oil through the liquid delivery tube, so that the hydraulic oil in the external liquid storage device flows into the triaxial cell through the second oil port, and then flows into the container through a third through hole of the device. Wherein a height of the hydraulic oil flowing into the container exceeds the height of the third through hole in the device but does not exceed the height of the lower end cap installed within the container. Therefore, the high-pressure gas in the device can be prevented from leaking into the triaxial cell, and the contact between the hydraulic oil and the core sample can also be avoided.

During the application of the device, system and method for triaxial compression test with/without jacket by gas confining pressure on rock provided by the present disclosure, the device for triaxial compression test with/without jacket by gas confining pressure on rock gases is installed in the triaxial cell, the device includes the container, the accommodating cavity is disposed in the container, the first through hole and the second through hole are respectively disposed at the upper end of the container, and the third through hole is disposed at the lower end of the side wall of the container. After the core sample is placed in the accommodating cavity, the hydraulic oil is injected into the space between the triaxial cell and the container, the gas inlet and outlet of the triaxial cell is connected with the air inflation and pressurization device, the container is inflated through the air inflation and pressurization device, the gas inlet and outlet, the communicating tube and the second through hole so as to apply the confining pressure with the preset value on the core sample. In this way, the internal pressure applied by the high-pressure gas on the near field surrounding rock of the salt cavern can be accurately simulated, and the triaxial compression test with/without jacket by gas confining pressure on rock is achieved. Moreover, as the device is provided with the third through hole used for communicating the accommodating cavity with the triaxial cell, the pressure balance between the accommodating cavity and the triaxial cell is kept so as to transfer the pressure of the high pressure gas injected into the accommodating cavity to the hydraulic oil in the triaxial cell, so that the triaxial cell bears the pressure, which is not only conducive to reducing the design difficulty of the device, but also conducive to prolonging the service life of the device.

In order that the above objectives, features and advantages of the present disclosure are more obvious and easy to understand, a detailed description is given below by the following preferred embodiments in combination with appended drawings.

BRIEF DESCRIPTION OF THE DRAWINGS

To illustrate technical solutions in the embodiments of the present disclosure more clearly, the drawings which are needed in the description of the embodiments are briefly introduced. Apparently, the drawings in the description below are merely some of the embodiments of the present disclosure, based on which other drawings can be obtained by those of ordinary skill in the art without any creative effort.

Figure 1:
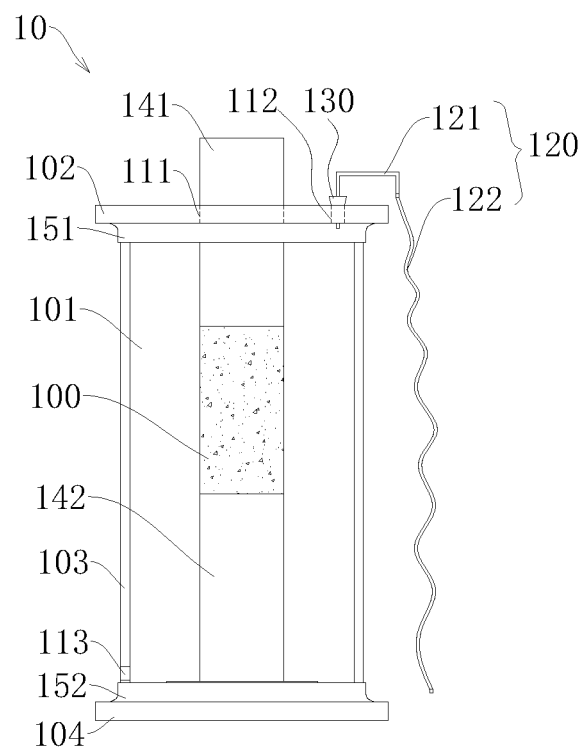
FIG. 1 shows a structural schematic diagram of a device for triaxial compression test with/without jacket by gas confining pressure on rock in accordance with an embodiment of the present disclosure.

Reference numbers are respectively as follows: system 1; device 10; core sample 100; accommodating cavity 101; cover plate 102; side wall 103; lower platen 104; lower platen body 1041; tray 1042; locating pin 1043; first through hole 111; second through hole 112; third through hole 113; communicating tube 120; first connecting tube 121; second connecting tube 122; first rubber stopper with a hole 130; upper end cap 141; lower end cap 142; first annular sealing element 151; second annular sealing element 152; rubber ring 160; triaxial cell 20; gas inlet and outlet 201; second rubber stopper with a hole 202; conduit 203; axial force loading end cap 210; intake tube 221; gas port valve 222; first oil port 231; first switch valve 232; second oil port 241; second switch valve 242; air inflation and pressurization device 300; liquid delivery tube 410; external liquid storage device 420; hydraulic oil 500; and gas 600.

DETAILED DESCRIPTION OF THE INVENTION

The technical solutions of the present invention will be described in detail below with reference to the drawings and specific embodiments. It should be understood that the embodiments of the present invention and specific features in the embodiments are detailed descriptions of the technical solutions of the present invention, but not limitations to the technical solutions of the present invention. In the case of no conflict, the embodiments of the present invention and technical features in the embodiments can be combined with each other.

In the description of the present invention, it should also be noted that, the terms "dispose", "install" and "connect" should be interpreted broadly unless explicitly stated or limited otherwise. For example, the "connect" can be a direct connection, can also be an indirect connection through an intermediary, and can also be internal communication of two elements. Those of ordinary skill in the art can understand the specific meanings of the above terms in the present invention according to specific circumstances.

Herein, relational terms such as first and second and the like are only used for distinguishing one entity or operation from another entity or operation, and do not necessarily require or imply that there is any actual relationship or sequence between these entities or operations. Moreover, the terms "comprise", "include" and any other variations thereof are intended to cover non-exclusive inclusion, such that a process, method, article or device including a series of factors not only includes those factors, but also includes other factors that are not explicitly listed, or further includes all inherent factors of this process, method, article or device. In the absence of any more limitation, a factor defined by a sentence "includes a . . . " does not exclude the existence of other same factors in the process, method, article or device including the factor.

It should be noted herein that A/B represents A or B, that is, it can be either A or B. For example, "triaxial compression test with/without jacket" means that it can be either with jacket or without jacket. The "device for triaxial compression test with/without jacket by gas confining pressure on rock" indicates that the device is applicable not only to a triaxial compression test with jacket by gas confining pressure on rock, but also to a triaxial compression test without jacket by gas confining pressure on rock.

In an actual engineering, no matter salt caverns for underground gas storage or compressed air energy storage, underground salt caverns are all filled with high-pressure gas. Therefore, it is particularly important to test the mechanical deformation and strength characteristics of rocks under the high-pressure gas for evaluating the engineering stability of the salt caverns for underground gas storage or compressed air energy storage. In the prior art, there is no test equipment for this case, and a triaxial compression test with/without jacket by gas confining pressure on rock cannot be achieved. The present invention provides a device for triaxial compression test with/without jacket by gas confining pressure on rock, which is applied for a system for triaxial compression test with/without jacket by gas confining pressure on rock. The system further includes a triaxial cell. By cooperating the device with the triaxial cell, an internal pressure applied by the high pressure gas on the near field surrounding rock of a salt cavern can be accurately simulated, and a triaxial compression test with/without jacket by gas confining pressure on rock is achieved to evaluate the mechanical characteristics of rocks under the action of the high pressure gas.

It should be noted that the device for triaxial compression test with/without jacket by gas confining pressure on rock in accordance with the embodiment of the present invention can not only be used for realizing a triaxial compression test with jacket by gas confining pressure on rock, but also for realizing a triaxial compression test without jacket by gas confining pressure on rock. The triaxial compression test with jacket means that during the test, a core sample is wrapped by a protective sleeve such as a heat-shrinkable tube, so that the confining pressure applied on the core sample may be directly transferred to the protective sleeve that is only wrapped on the surface of the core sample, and then the protective sleeve transfers the confining pressure to the core sample. While the triaxial compression test without jacket means that the protective sleeve on the surface of the core sample in an ordinary triaxial compression test is removed, and the protective sleeve usually uses the heat-shrinkable tube, such that the core sample is in direct contact with the high-pressure gas, and then the mechanical characteristics of the rocks under the action of the high pressure gas are disclosed relatively accurately. The embodiments of the present invention are mainly illustrated by taking the triaxial compression test without jacket by gas confining pressure on rock as an example.

Referring to FIG. 1, an embodiment of the present invention provides a device 10 for the triaxial compression test with/without jacket by gas confining pressure on rock, including: a container provided with an accommodating cavity 101 therein for placing a core sample 100. As shown in FIG. 1, a first through hole 111 and a second through hole 112 are respectively disposed at an upper end of the container, and a third through hole 113 is disposed at a lower end of a side wall 103 of the container.

In some embodiments, the first through hole 111 is for the end cap for loading an axial pressure to the core sample 100 to penetrate through. The word "penetrate through" can also be understood as connection. When in use, the end cap for loading the axial pressure to the core sample 100 passes through the first through hole 111 to be connected with the core sample 100. It can be understood that the first through hole 111 is disposed in a central position of a cover plate 102 of the container. In the present embodiment, an axial force loading end cap in the triaxial cell can directly pass through the first through hole 111 for loading the axial pressure to a sample 100 placed in the accommodating cavity 101. For convenient design and installation of the device 10, another assorted end cap can also be additionally designed, and an outside diameter of the assorted end cap is matched with an aperture of the first through hole 111. In a test, one end of the assorted end cap passes through the first through hole 111 to be in contact with one end of the core sample 100, and the other end thereof is used as a pressure bearing surface of the axial force. The axial force loading end cap within the triaxial cell applies the axial pressure on the core sample 100 through the assorted end cap.

The second through hole 112 is used for injecting a gas into the accommodating cavity 101 so as to apply a confining pressure on the core sample 100 by the gas entering the accommodating cavity 101. In some embodiments, an amount of the injected gas can be controlled according to a magnitude of the confining pressure required. The injected gas is selected according to actual needs. For example, when it needs to simulate internal pressure applied by natural gas on the near field rock wall of the salt cavern for storing the natural gas, the gas injected into the accommodating cavity 101 is high-pressure natural gas. In other application scenes, the gas can also be high-pressure air or high-pressure nitrogen or the like.

In a process of a triaxial compression test with/without jacket by gas confining pressure on rock by using the device 10 and the assorted triaxial cell, the third through hole 113 in the device 10 is used for communicating the accommodating cavity 101 with the triaxial cell, so that the pressures within the accommodating cavity 101 and the triaxial cell are always balanced. In other words, the pressure within the accommodating cavity 101 is the same as the pressure with the triaxial cell, thus the container does not need to bear any pressure difference, and all the pressure is borne by the triaxial cell, which is conducive to prolonging a service life of the device 10. In addition, the design of the communication between the inside and the outside of the container also reduces sealing requirements for the device 10, no precise seal is required, and an ordinary seal can meet the requirements, thus a design difficulty of the device 10 is reduced.

In addition, in the triaxial compression test with/without jacket by gas confining pressure on rock, in order to monitor a strain of the core sample 100, a strain gauge for detecting the strain may be installed on the core sample 100. Therefore, the third through hole 113 is further used for being passed through by a connection line of the strain gauge to facilitate the wiring of the strain gauge. The connection line of the strain gauge on the core sample 100 can be connected with a jack in the lower platen of the triaxial cell through the third through hole 113.

On the basis of this, in the present embodiment, one or more third through holes 113 can be provided, for example, 1-4 third through holes 113 can be provided. The number of the third through holes 113 can be specifically determined according to actual needs.

It can be understood that, in order to conveniently inject the gas into the accommodating cavity 101 through the second through hole 112 of the device 10 during the test to apply the confining pressure to a circumferential direction of the core sample 100 by the high pressure gas, a through hole is needed to be provided on the triaxial cell assorted with the device 10 for the triaxial compression test with/without jacket by gas confining pressure on rock in accordance with the present embodiment to serve as a gas inlet and outlet 201. The gas inlet and outlet 201 is in communication with the second through hole 112 on the device 10 through a gas delivery tube so as to inject the gas into the accommodating cavity 101 of the device 10 by an external air inflation and pressurization device 300 connected with the gas inlet and outlet 201, for example, a high pressure gas cylinder, until the pressure within the accommodating cavity 101 reaches a specified confining pressure.

To simplify the installation of the device 10, the device 10 for the triaxial compression test with/without jacket by gas confining pressure on rock in accordance with the present embodiment can further include a communicating tube 120, as shown in FIG. 1. One end of the communicating tube 120 is in sealed fit with the second through hole 112 and in communication with the accommodating cavity 101 of the container, and the other end of the communicating tube 120 is used for connecting the gas inlet and outlet provided on the triaxial cell. The communicating tube 120 is used as a gas delivery tube between the gas inlet and outlet of the triaxial cell and the accommodating cavity 101 of the device 10. In a test, the other end of the communicating tube 120 is connected with the gas inlet and outlet provided on the triaxial cell, such that the gas can be injected into the gas inlet and outlet of the triaxial cell by the external air inflation and pressurization device 300, for example, the high pressure gas cylinder, and the gas enters the accommodating cavity 101 after passing through the gas inlet and outlet, the communicating tube 120 and the second through hole 112 in sequence.

In some embodiments, one end of the communicating tube 120 and the second through hole 112 have various sealed fit manners. As an embodiment, a sealing ring can be provided within the second through hole 112, and one end of the communicating tube 120 is inserted in the second through hole 112 with the sealing ring to realize the sealed fit with the second through hole 112. As another embodiment, the device 10 further includes a first rubber stopper with a hole 130, as shown in FIG. 1, and one end of the communicating tube 120 is in sealed fit with the second through hole 112 through the first rubber stopper with a hole 130. At this time, one end of the communicating tube 120 is inserted in the hole of the first rubber stopper with a hole 130 to be in communication with the accommodating cavity 101. As the rubber stopper is made of rubber, and the rubber is a damping material, thus there is a greater friction force between the first rubber stopper with a hole 130 made of rubber and the second through hole 112, and there is also a greater friction force between the hole in the first rubber stopper with a hole 130 and an outer wall of the communicating tube 120 as well, thus a sealing effect is better.

In some embodiments, as shown in FIG. 1, the communicating tube 120 can include a first connecting tube 121 and a second connecting tube 122. One end of the first connecting tube 121 is in sealed fit with the second through hole 112, and the other end of the first connecting tube 121 is connected with one end of the second connecting tube 122. The other end of the second connecting tube 122 is used for connecting the gas inlet and outlet provided in the triaxial cell.

As an embodiment, the first connecting tube 121 can be a U-shaped tube, and one end of the U-shaped tube is in sealed fit with the second through hole 112. In some embodiments, the U-shaped tube may be made of organic resin glass, but is not limited thereto and is preferably made of a transparent material. When one end of the U-shaped tube is in sealed fit with the second through hole 112 through the first rubber stopper with a hole 130, the outside diameter of the U-shaped tube should be matched with the first rubber stopper with a hole 130, and the outside diameter of the U-shaped tube cannot be smaller than an inner hole of the first rubber stopper with a hole 130 and cannot be too large, so that the U-shaped tube can be inserted in the first rubber stopper with a hole 130 and can be closely combined. In addition, to conveniently connect the gas inlet and outlet on the triaxial cell through the second connecting tube 122, a length of the bottom part of the U-shaped tube is greater than the shortest distance between the second through hole 112 of the cover plate 102 and an edge of the cover plate 102, so that the other end of the U-shaped tube can stretch out from the edge of the cover plate 102 of the container.

As an embodiment, the second connecting tube 122 can adopt a rubber tube. The rubber tube has characteristics such as pressure resistance, acid and alkali resistance, strong resilience, high transparency and the like.

Figure 2:
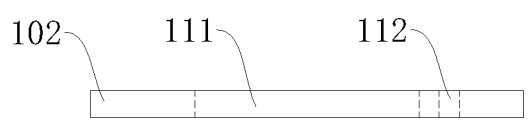
FIG. 2 shows a structural schematic diagram of a cover plate of a device for triaxial compression test with/without jacket by gas confining pressure on rock in accordance with an embodiment of the present disclosure at a first angle of view.
Figure 3:
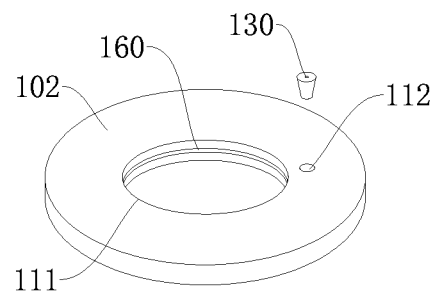
FIG. 3 shows a structural schematic diagram of a cover plate of a device for triaxial compression test with/without jacket by gas confining pressure on rock in accordance with an embodiment of the present disclosure at a second angle of view.

In addition, as an optional embodiment, the cover plate 102, the lower platen 104 and the side wall 103 of the container can be separately disposed, and the cover plate 102 and the lower platen 104 can be respectively in sealed fit with the side wall 103. In this case, the cover plate 102, the lower platen 104 and the side wall 103 can be separately shaped. As shown in FIG. 2 and FIG. 3, the first through hole 111 and the second through hole 112 are respectively provided on the cover plate 102, the first through hole 111 is disposed in the center of the cover plate 102, and the third through hole 113 is disposed in the bottom of the side wall 103. In a test, the cover plate 102, the lower platen 104, and the side wall 103 are assembled to form the container.

Figure 4:
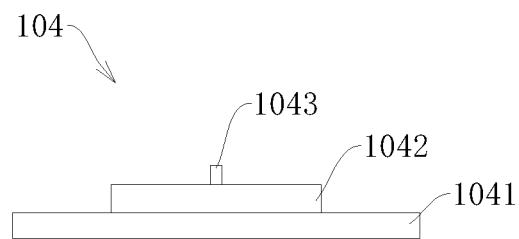
FIG. 4 shows a structural schematic diagram of a lower platen of a device for triaxial compression test with/without jacket by gas confining pressure on rock in accordance with an embodiment of the present disclosure at a third angle of view.
Figure 5:
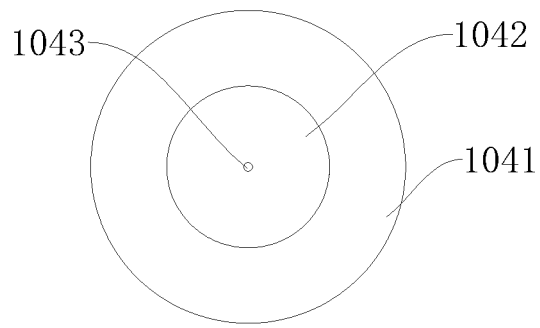
FIG. 5 shows a structural schematic diagram of a lower platen of a device for triaxial compression test with/without jacket by gas confining pressure on rock in accordance with an embodiment of the present disclosure at a fourth angle of view.

Further, to conveniently place and fix the core sample 100, as shown in FIG. 4 and FIG. 5, the lower platen 104 can include a lower platen body 1041 and a tray 1042. The tray 1042 is disposed above the lower platen body 1041, and a locating pin 1043 is disposed on the tray 1042. As an embodiment, the locating pin 1043 can be disposed at a central position of the tray 1042.

Figure 6:
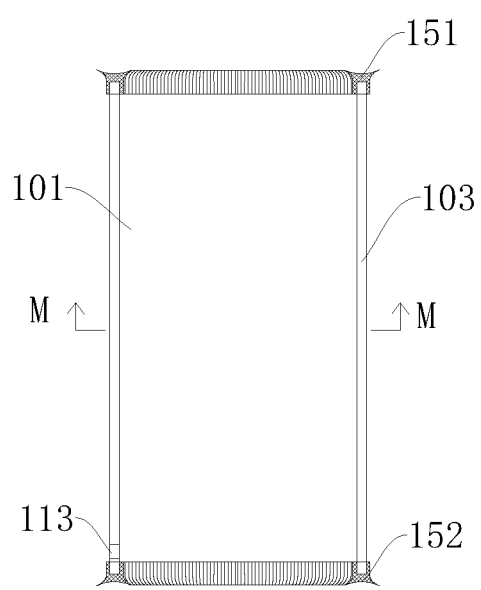
FIG. 6 shows a structural schematic diagram of a portion of a device for triaxial compression test with/without jacket by gas confining pressure on rock in accordance with an embodiment of the present disclosure.
Figure 7:
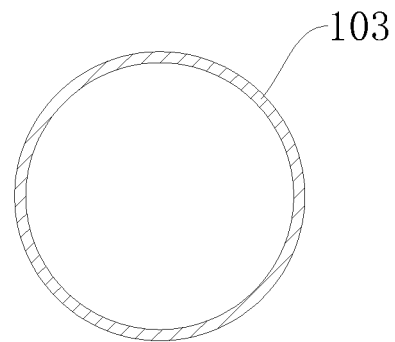
FIG. 7 shows an M-M sectional view of FIG. 6.

In some embodiments, according to the needs of the test on different parts of the container, more suitable materials can be selected respectively. In the present embodiment, the material of the lower platen 104 and the cover plate 102 can be preferably stainless steel to prevent corrosive rocks, such as salt rocks, after being cracked and scattered, from corroding the device. As shown in FIG. 6 and FIG. 7, the side wall 103 of the container is cylindrical. In order to facilitate observing a condition within the device 10 during the test, the side wall 103 of the container is preferably made of a transparent material. Moreover, since the accommodating cavity 101 of the container is in communication with the triaxial cell in the test, the side wall 103 of the container does not need to bear a pressure. Therefore, in an embodiment, the side wall 103 of the container can be made of organic resin glass.

In an optional embodiment, the device 10 for the triaxial compression test with/without jacket by gas confining pressure on rock may further include a first annular sealing element 151 and a second annular sealing element 152, as shown in FIG. 6. One end of the side wall 103 is in sealed fit with the cover plate 102 through the first annular sealing element 151, and the other end of the side wall 103 is in sealed fit with the lower platen 104 through the second annular sealing element 152. In an embodiment, the first annular sealing element 151 and the second annular sealing element 152 are both annular suction cups, at this time, an upper end and a lower end of the side wall 103 are respectively connected with one annular suction cup, the lower platen 104 and the annular suction cup on the lower end of the side wall 103 are connected in an adsorption manner, and the cover plate 102 and the annular suction cup on the upper end of the side wall 103 are connected in an adsorption manner. In some embodiments, the annular suction cup can be made of a rubber material.

Figure 8:
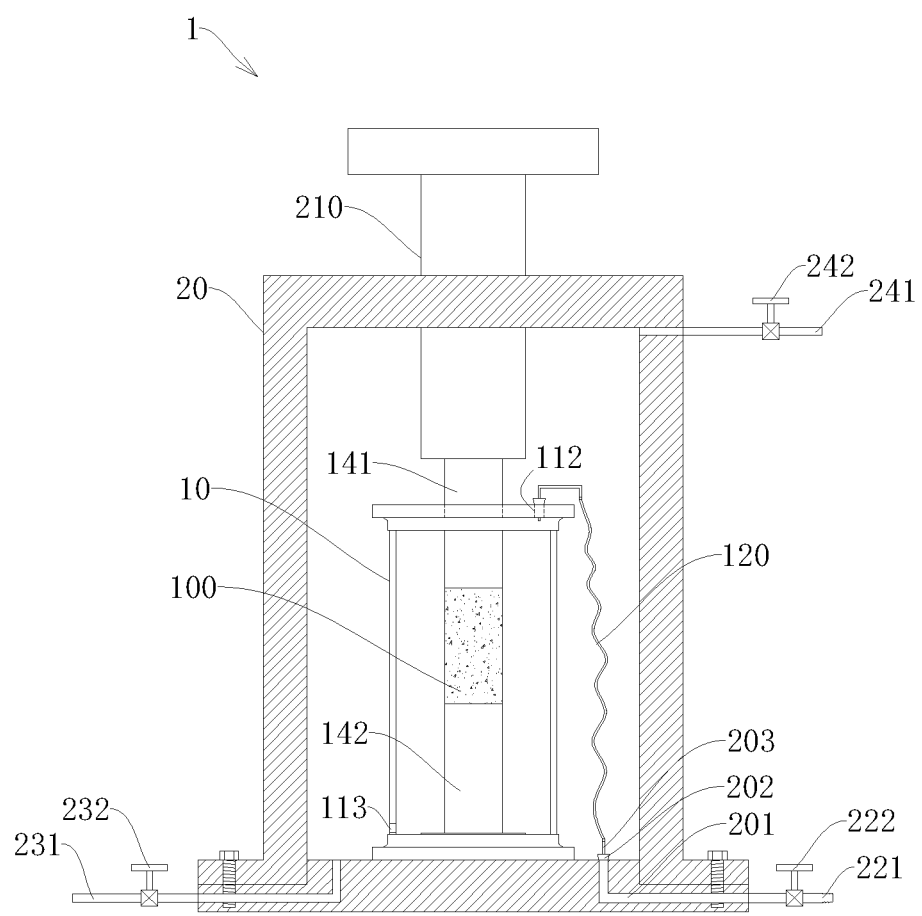
FIG. 8 shows a structural schematic diagram of a system for triaxial compression test with/without jacket by gas confining pressure on rock in accordance with an embodiment of the present disclosure.

In an optional embodiment, the device 10 for the triaxial compression test with/without jacket by gas confining pressure on rock further includes an upper end cap 141. One end of the upper end cap 141 is used for connecting a top end of the core sample 100, and the other end of the upper end cap 141 passes through the first through hole 111 to serve as an axial pressure bearing surface to bear an axial pressure applied by an axial force loading end cap 210 of the triaxial cell 20, as shown in FIG. 8. In this case, one end of the upper end cap 141 serving as the axial pressure bearing surface can be very smooth through a processing technique so as to avoid the generation of component forces in other directions excluding a vertical direction while bearing an axial pressure, and thus test data are more accurate.

In an optional embodiment, the device 10 for the triaxial compression test with/without jacket by gas confining pressure on rock may further include a lower end cap 142. One end of the lower end cap 142 is used for connecting the lower platen 104 of the container, and the other end of the lower end cap 142 is used for connecting a bottom end of the core sample 100. In an embodiment, one end of the lower end cap 142 used for connecting the lower platen 104 is provided with a blind hole to serve as a locating hole. A specification of the locating hole corresponds to a specification of the locating pin 1043 provided on the lower platen 104. By means of the cooperation of the locating hole and the locating pin 1043 on the lower platen 104, a position of the lower end cap 142 can be fixed so as to fix the position of the core sample 100. In this way, when the core sample 100 is subjected to the high-pressure gas, the core sample 100 may not move or tilt.

The device 10 for the triaxial compression test with/without jacket by gas confining pressure on rock in accordance with the embodiment of the present invention when being applied is installed within the triaxial cell 20, as shown in FIG. 8. The gas is injected into the accommodating cavity 101 through the second through hole 112 so as to apply the confining pressure on the core sample 100 with the gas, which can simulate more accurately the internal pressure applied by the high pressure gas on the near field rock wall of the salt cavern, achieving the triaxial compression test with/without jacket by gas confining pressure on rock. Moreover, as the device 10 is provided with a third through hole 113 for communicating the accommodating cavity 101 with the triaxial cell 20, which functions as keeping a pressure balance between the accommodating cavity 101 and the triaxial cell 20, so that the pressure of the high pressure gas injected into the accommodating cavity 101 is transferred to hydraulic oil 500 within the triaxial cell 20, and the triaxial cell 20 bears the pressure, thereby being not only conducive to reducing a design difficulty of the device 10, but also to prolonging a service life of the device 10.

Referring to FIG. 8, an embodiment of the present invention further provides a system 1 for the triaxial compression test with/without jacket by gas confining pressure on rock, including a triaxial cell 20 and the device 10 for the triaxial compression test with/without jacket by gas confining pressure on rock mentioned above. As shown in FIG. 8, the device 10 is installed within the triaxial cell 20.

In some embodiments, a gas inlet and outlet 201 is disposed on a lower platen of the triaxial cell 20, the gas inlet and outlet 201 is used for connecting an external air inflation and pressurization device 300, and the gas inlet and outlet 201 is in communication with a second through hole 112 of the device 10 through a communicating tube 120.

In some embodiments, a second rubber stopper with a hole 202 is disposed at an inner end of the gas inlet and outlet 201, an outer wall of the second rubber stopper with a hole 202 is in sealed fit with an inner wall of the gas inlet and outlet 201, a conduit 203 in sealed fit with the hole of the second rubber stopper with a hole 202 is disposed in the hole, and the communicating tube 120 is in communication with the gas inlet and outlet 201 through the conduit 203.

To conveniently control an inflation and deflation of the device 10, an intake tube 221 stretching out from the triaxial cell 20 is disposed at an outer end of the gas inlet and outlet 201, and a gas port valve 222 for controlling a connection and disconnection of the intake tube 221 is disposed on the intake tube 221. In the present embodiment, the air inflation and pressurization device 300 can be a high pressure gas cylinder.

It should be noted that the triaxial cell 20 is more common in a test machine. A first oil port 231 is disposed on the lower platen of the triaxial cell 20, a first switch valve 232 for controlling an opening and closing of the first oil port 231 is disposed at the first oil port 231, and the first oil port 231 is used for connecting a hydraulic system of the test machine; and a second oil port 241 is further disposed at the upper end of the triaxial cell 20, and a second switch valve 242 for controlling an opening and closing of the second oil port 241 is disposed at the second oil port 241.

Figure 9:
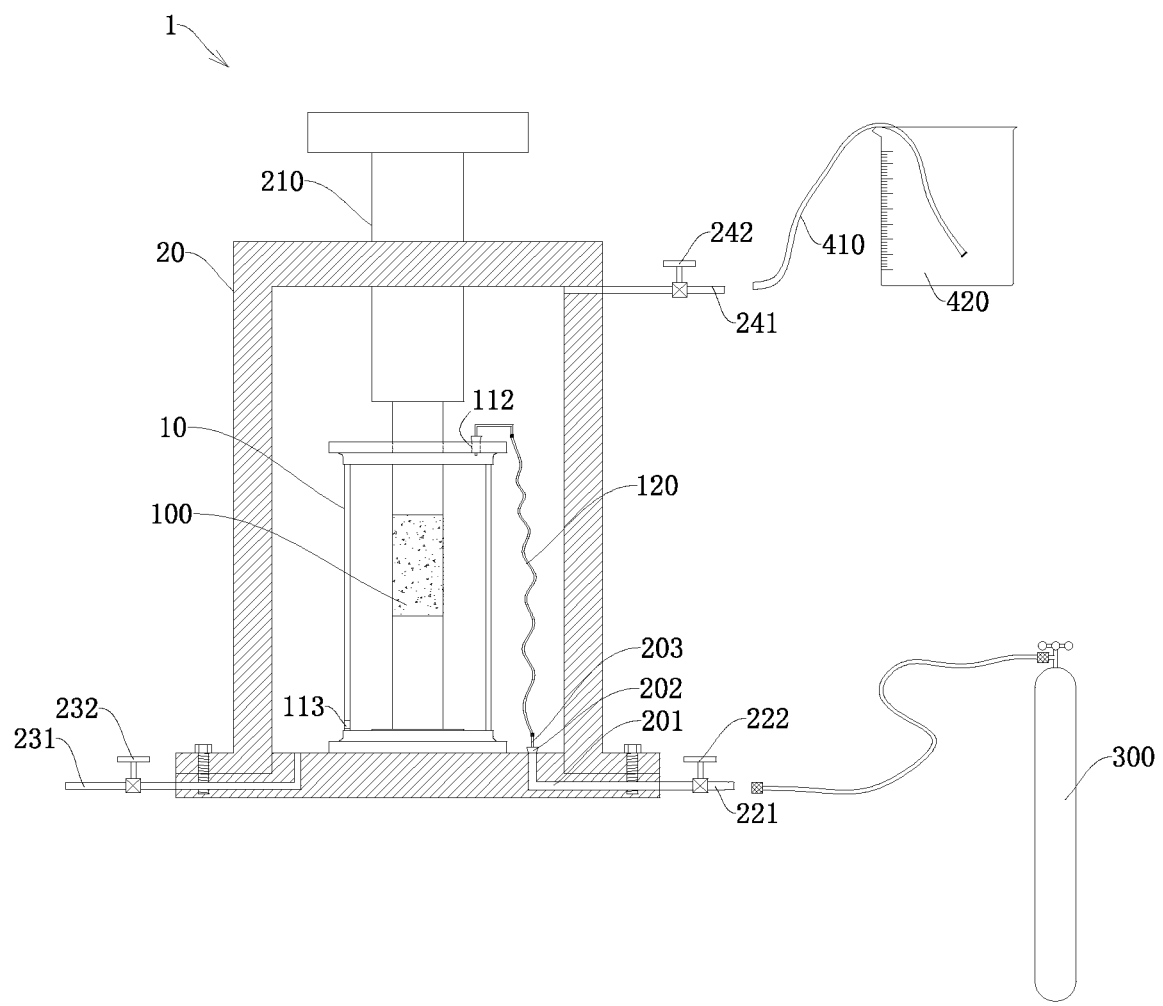
FIG. 9 shows another structural schematic diagram of a system for triaxial compression test with/without jacket by gas confining pressure on rock in accordance with an embodiment of the present disclosure.

In addition, to conveniently discharge gas and return oil in the triaxial compression test with/without jacket by gas confining pressure on rock, the above system 1 further includes an external liquid storage device 420 and a liquid delivery tube 410, as shown in FIG. 9. The external liquid storage device 420 is used for storing hydraulic oil 500, one end of the liquid delivery tube 410 is in communication with the second oil port 241 of the triaxial cell 20, and the other end of the liquid delivery tube 410 is immersed into the hydraulic oil 500 within the external liquid storage device 420. In some embodiments, the external liquid storage device 420 is preferably a transparent container with scales, for example, a beaker to conveniently be knowledge of an amount of the hydraulic oil 500 within the external liquid storage device 420. The liquid delivery tube 410 can be a transparent rubber tube to conveniently observe a transmission condition of the hydraulic oil 500. A specific method for using the external liquid storage device 420 and the liquid delivery tube 410 will be described in corresponding methods embodiment below.

Figure 10:
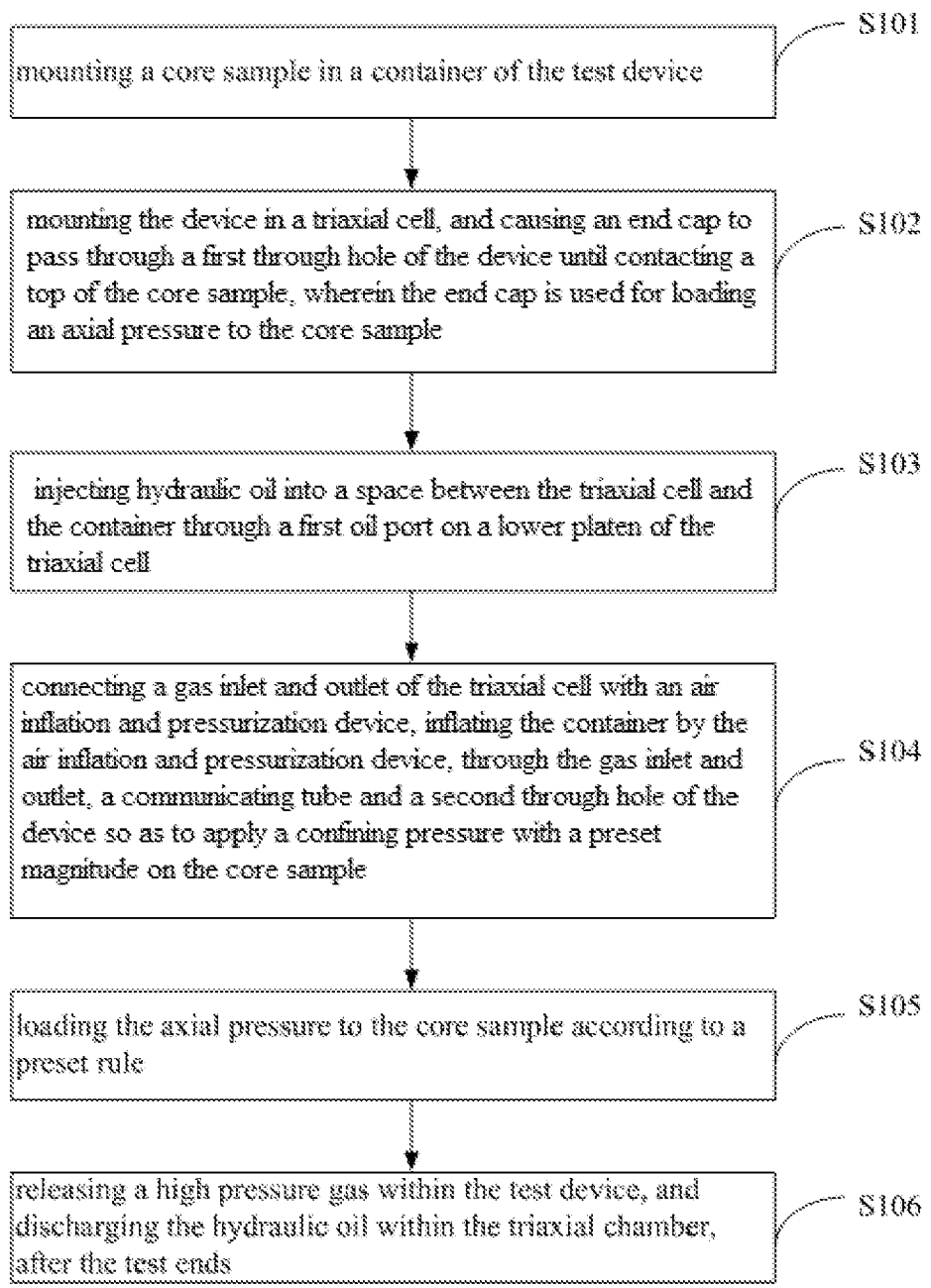
FIG. 10 shows a method flowchart of a method for the triaxial compression test with/without jacket by gas confining pressure on rock in accordance with an embodiment of the present disclosure.

Referring to FIG. 10, it is a method flowchart of a method for the triaxial compression test with/without jacket by gas confining pressure on rock in accordance with an embodiment of the present invention, the method is implemented on the basis of the device 10 for the triaxial compression test with/without jacket by gas confining pressure on rock mentioned above, and can be not only used for realizing a triaxial compression test without jacket by gas confining pressure on rock, but also can be used for realizing a triaxial compression test with jacket by gas confining pressure on rock. As shown in FIG. 10, the method includes:

step S101, mounting a core sample within a container of the device;

step S102, mounting the device in a triaxial cell, and causing a end cap to pass through a first through hole of the device until contacting a top of the core sample, wherein the end cap is used for loading an axial pressure to the core sample;

step S103, injecting hydraulic oil into a space between the triaxial cell and the container through a first oil port on a lower platen of the triaxial cell;

step S104, connecting a gas inlet and outlet of the triaxial cell with an air inflation and pressurization device, inflating the container by the air inflation and pressurization device, through the gas inlet and outlet, a communicating tube and a second through hole of the device so as to apply a confining pressure with a preset magnitude on the core sample;

step S105, loading an axial pressure to the core sample according to a preset rule;

step S106, releasing a high pressure gas within the device and discharging the hydraulic oil within the triaxial cell, after a test ends.

In some embodiments, step S101 is a step of placing the core sample 100, and step S102 is a step of mounting the device 10. As various components of the device 10 are separately disposed, which can be accomplished in a process of assembling the device 10.

For example, in a specific application scenario, the lower platen 104 of the device 10, that is, the lower platen 104 of the container, can be placed on the lower platen of the triaxial cell 20 at first, and a concentricity of the two is ensured by a locating pin and a locating hole; the lower end cap 142 is installed on the lower platen 104 of the container, and the concentricity is also ensured by the locating pin and the locating hole; the core sample 100 with a strain gauge installed is placed on the lower end cap 142; the upper end cap 141 is placed on the core sample; the side wall 103 of the container and the annular suction cups on the two ends are assembled; the cover plate 102 of the container is adsorbed onto the annular suction cup at the upper end of the side wall 103; the upper end cap 141 passes through the first through hole 111 on the cover plate 102, and a circuit connecting line of the strain gauge passes through the third through hole 113 in the bottom of the side wall 103 of the container, and the annular suction cup at the lower end of the side wall 103 is pressed on the lower platen 104 on the container.

It should be noted that the device 10 can be assembled in a slightly different order, as long as it is assembled.

It should also be noted that for the triaxial compression test with jacket, the core sample 100 needs to be wrapped by a protective sleeve such as a heat-shrinkable tube. For the triaxial compression test without jacket, the core sample 100 does not need to be wrapped by a protective sleeve, so that the core sample 100 directly contacts the high-pressure gas.

Step S103 is an oil filling process. A space between the triaxial cell 20 and the container is filled with aviation hydraulic oil 500 by a hydraulic system. In some embodiments, the oil filling process includes:

firstly, the gas inlet and outlet 201 in the bottom of the triaxial cell 20 is closed. For example, in the case that a gas valve is disposed at the gas inlet and outlet 201, the gas valve is closed so that the aviation hydraulic oil 500 cannot enter into the container through the third through hole 113 at the side wall 103 of the container.

Figure 11:
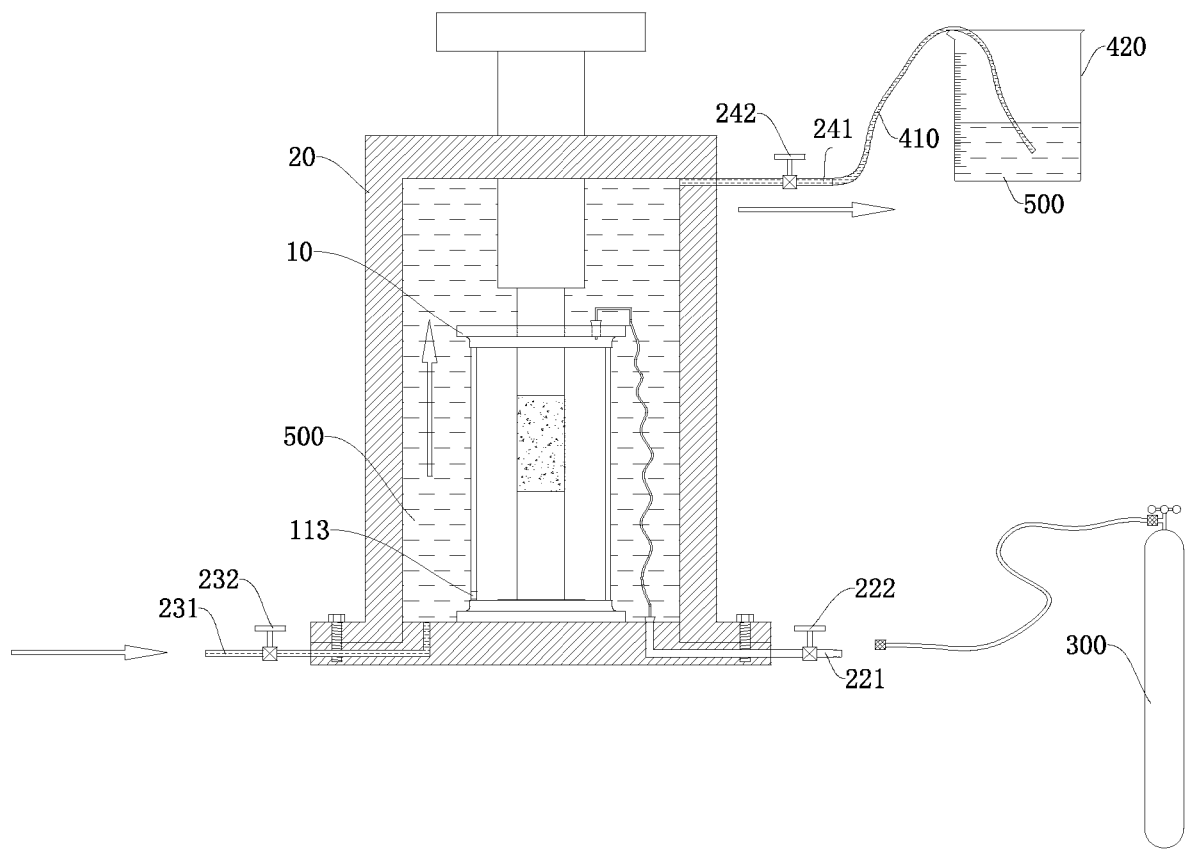
FIG. 11 shows a state schematic diagram of an oil injection process of a triaxial compression test with/without jacket by gas confining pressure on rock in accordance with an embodiment of the present disclosure.

Then, the oil is injected into the space between the triaxial cell 20 and the container by the hydraulic system through the first oil port 231 in the lower platen of the triaxial cell 20, until the space between the triaxial cell 20 and the container is fully filled, as shown in FIG. 11. It should be noted that, transverse short line segments distributed in FIG. 11 represent the hydraulic oil 500. For the convenience of observation, a transparent rubber tube is connected to the second oil port 242 at the upper end of the triaxial cell 20. If it can be seen from the transparent rubber tube that the aviation hydraulic oil 500 flows out, it indicates that the space between the triaxial cell 20 and the container is fully filled with the hydraulic oil 500. At this time, a first switch valve 232 for controlling an opening and closing of the first oil port 231 is closed to stop injecting the oil.

Figure 13:
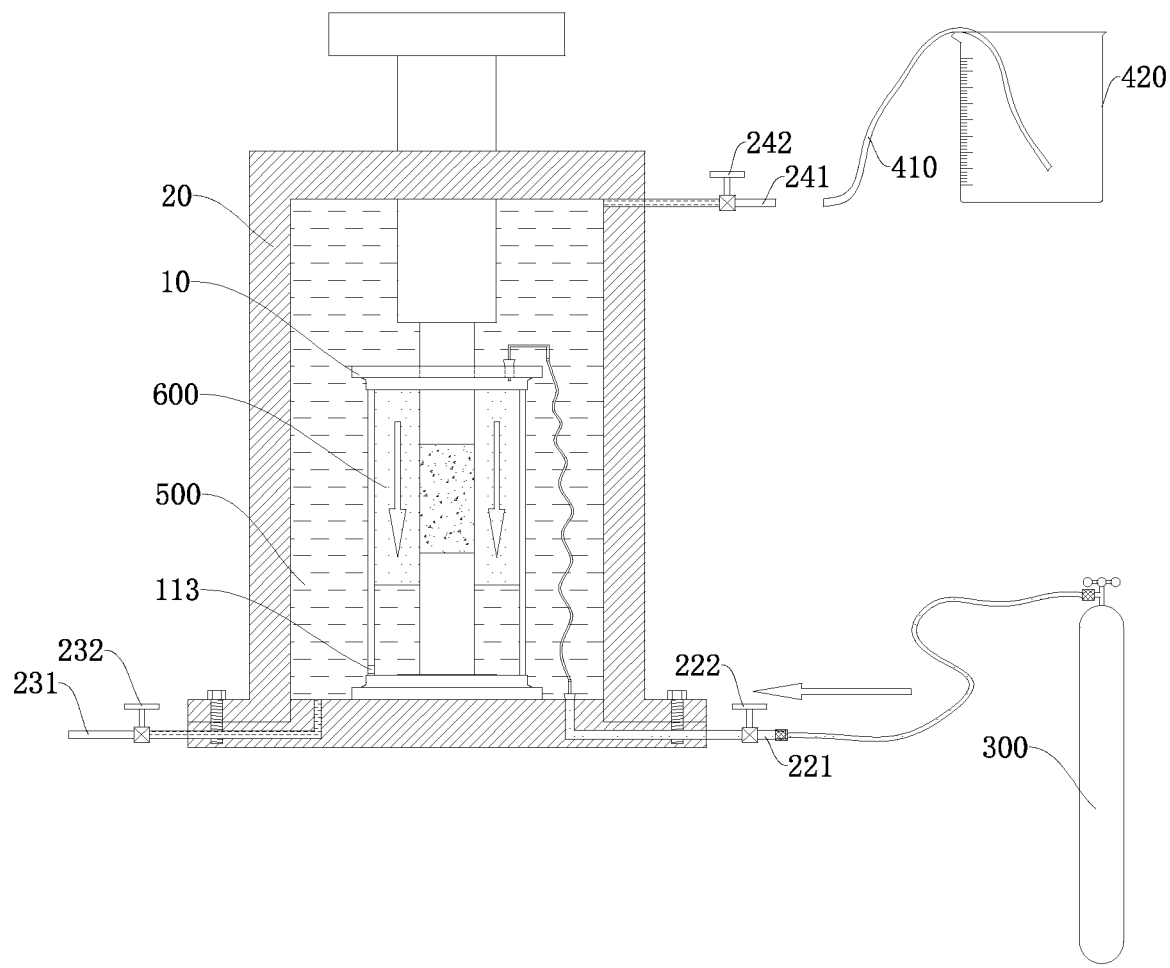
FIG. 13 shows a state schematic diagram of a gas pressurization process of a triaxial compression test with/without jacket by gas confining pressure on rock in accordance with an embodiment of the present disclosure.

Step S104 is a gas 600 pressurization process. As shown in FIG. 13, the high-pressure gas cylinder is connected to the gas inlet and outlet 201 on the lower platen of the triaxial cell 20, and a gas port valve 222 for controlling an opening and closing of the gas inlet and outlet 201 is opened to begin to inflate and pressurize the accommodating cavity 101 of the device 10. It should be noted that an array of black dot distributed in FIG. 13 represents the gas 600. Since the accommodating cavity 101 of the device 10 is in communication with the triaxial cell 20, the pressure in the accommodating cavity 101 is the same as the pressure in the triaxial cell 20. Thus the device 10 does not need to bear any pressure difference, and all the pressure is borne by the triaxial cell 20. It should be noted that the above gas 600 pressurization process can be realized by manually opening and closing the valve, and can also be achieved through a computer servo control system.

Step S105 is an axial pressure loading process. Because a loading principle of axial pressure is similar to that of other existing triaxial test processes, the specific axial pressure loading rules can refer to the existing triaxial test process, and will not be described in detail in the present embodiment.

Step S106 is a deflation and drainage process. After the axial pressure loading test is completed, a connection between the gas inlet and outlet 201 on the lower platen of the triaxial cell 20 and the high pressure gas cylinder is disconnected, and the gas port valve 222 is opened to release the high pressure gas 600 within the accommodating cavity 101 of the device 10. When the pressure is released to 1-2 MPa, the gas port valve 222 can be closed, and then the first oil port 231 on the lower platen of the triaxial cell 20 is opened, and the aviation hydraulic oil 500 is discharged under the gas confining pressure remained. Then, the triaxial cell 20 and the device 10 are sequentially opened, and the test ends.

According to the method for triaxial compression test with/without jacket by gas confining pressure on rock in accordance with the embodiment of the present invention, a confining pressure is applied on the core sample 100 within the device 10 by injecting the high pressure gas 600 into the device 10, thus the internal pressure applied by the high pressure gas 600 on the near field rock wall of the salt save can be effectively simulated, realizing the triaxial compression test with/without jacket by gas 600 pressure on rock and evaluating the mechanical characteristics of rocks under the high pressure gas 600.

Figure 14:
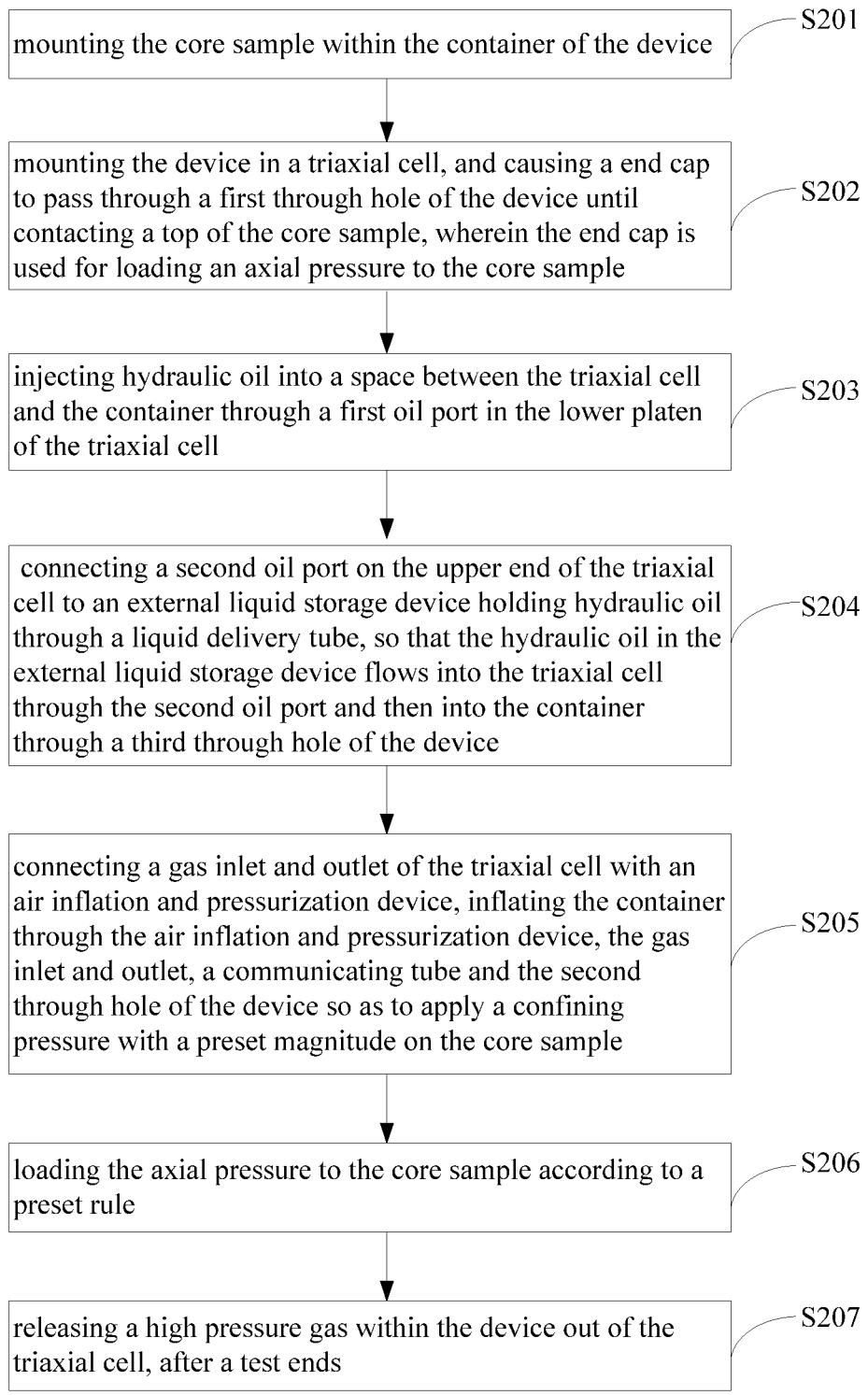
FIG. 14 shows another method flowchart of a method for the triaxial compression test with/without jacket by gas confining pressure on rock in accordance with an embodiment of the present disclosure.

Referring to FIG. 14, it is another flowchart of the method for triaxial compression test with/without jacket by gas confining pressure on rock in accordance with an embodiment of the present invention. The method is implemented on the basis of the device 10 for triaxial compression test with/without jacket by gas confining pressure on rock mentioned above, and can be not only used for realizing the triaxial compression test without jacket by gas confining pressure on rock, but also used for realizing the triaxial compression test with jacket by gas confining pressure on rock. A lower end cap 142 is installed within the container of the device 10, the core sample 100 is installed on the lower end cap 142, one end of the lower end cap 142 is connected with the lower platen 104 of the container, and the other end of the lower end cap 142 is connected to the bottom end of the core sample 100. As shown in FIG. 14, the method includes:

Step S201, mounting the core sample within the container of the device;

step S202, mounting the device in a triaxial cell, and causing a end cap to pass through a first through hole of the device until contacting a top of the core sample, wherein the end cap is used for loading an axial pressure to the core sample;

step S203, injecting hydraulic oil into a space between the triaxial cell and the container through a first oil port in the lower platen of the triaxial cell;

step S204, connecting a second oil port on the upper end of the triaxial cell to an external liquid storage device holding hydraulic oil through a liquid delivery tube, so that the hydraulic oil in the external liquid storage device flows into the triaxial cell through the second oil port and then into the container through a third through hole of the device; and wherein a height of the hydraulic oil 500 flowing into the container exceeds a height of the third through hole 113 in the device 10, and does not exceed the height of the lower end cap 142 installed within the container;

Step S205, connecting a gas inlet and outlet of the triaxial cell with an air inflation and pressurization device, inflating the container by the air inflation and pressurization device, through the gas inlet and outlet, a communicating tube and the second through hole of the device so as to apply a confining pressure with a preset magnitude on the core sample;

step S206, loading an axial pressure to the core sample according to a preset rule;

step S207, releasing a high pressure gas within the device out of the triaxial cell, after a test ends.

Compared with the method for triaxial compression test with/without jacket by gas confining pressure on rock as shown in FIG. 10, a gas deflation and oil return process is added between step S203 and step S205, namely step S204. As the gas deflation and oil return process is added, the high pressure gas within the device 10 can be prevented from leaking into the triaxial cell 20, and the contact between the hydraulic oil 500 and the core sample 100 can also be avoided.

In some embodiments, the gas deflation and oil return process can include:

the second oil port 241 on the upper end of the triaxial cell 20 is connected to a beaker containing the aviation hydraulic oil 500 by the liquid delivery tube 410, such as a transparent rubber tube, and the gas port valve 222 on the triaxial cell 20 is opened.

Figure 12:
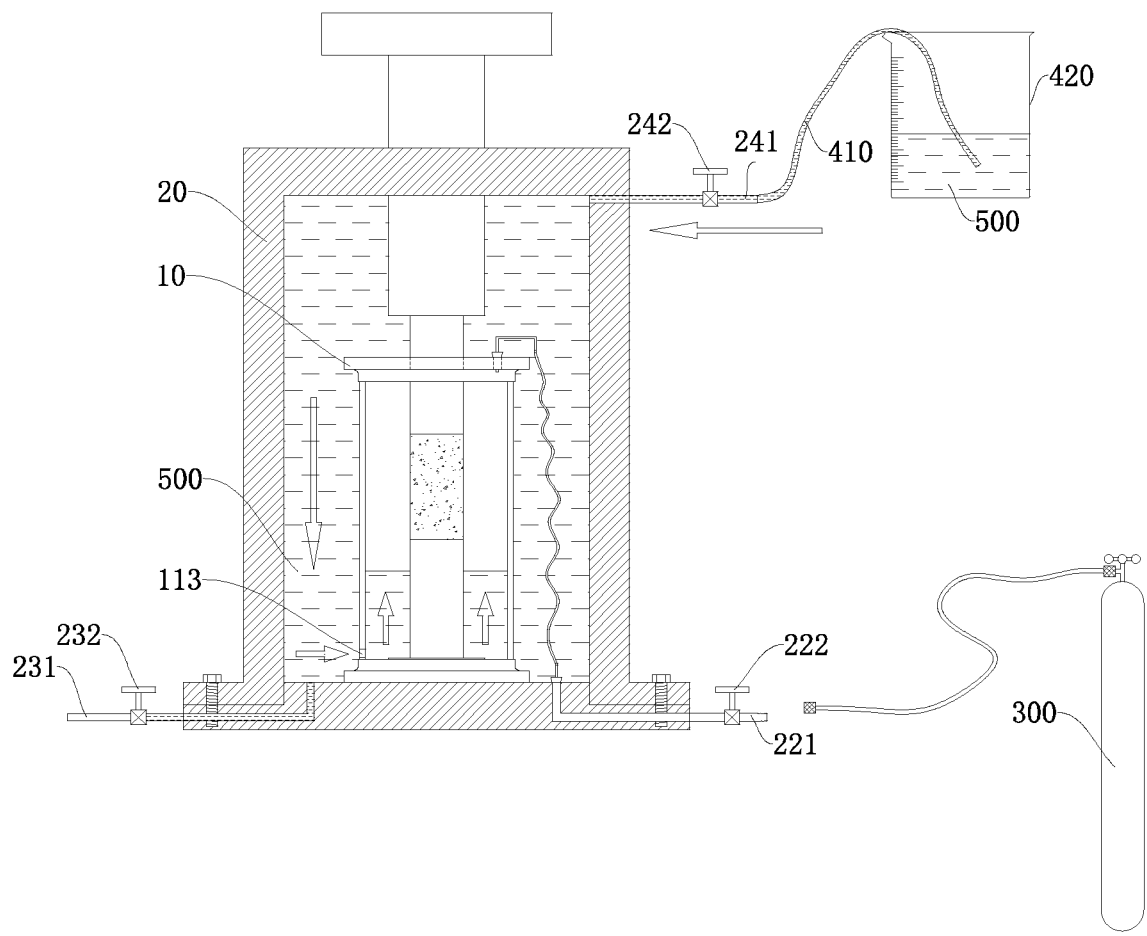
FIG. 12 shows a state schematic diagram of a deflation and oil return process of a triaxial compression test with/without jacket by gas confining pressure on rock in accordance with an embodiment of the present disclosure.

Due to gravity, the aviation hydraulic oil 500 in the beaker may flow into the triaxial cell 20 through the second oil port 241 of the upper end of the triaxial cell 20, and then into the accommodating cavity 101 through the third through hole 113 on the device 10, as shown in FIG. 12. In this way, the aviation hydraulic oil 500 in the beaker connected to the second oil port 241 of the upper end of the triaxial cell 20 may gradually decrease, and the reduced volume of the aviation hydraulic oil 500 within the beaker can be read out through the scales on the beaker, and the height of the aviation hydraulic oil 500 entering into the accommodating cavity 101 of the device 10 is calculated. The height of the aviation hydraulic oil 500 entering into the accommodating cavity 101 is kept close to the height of the lower end cap 142 disposed within the accommodating cavity 101, but not beyond the height of the lower end cap 142, thereby preventing the aviation hydraulic oil 500 from contacting the core and exceeding the height of the third through hole 113 on the device 10. A portion of the aviation hydraulic oil 500 allowed to enter into the accommodating cavity 101 of the device 10 aims to prevent the high-pressure gas from leaking into the triaxial cell 20 from the accommodating cavity 101 of the device 10.

The gas port valve 222 on the triaxial cell 20 is closed, and the second switch valve 242 at the second oil port 241 of the upper end of the triaxial cell 20 is closed, and then the gas deflation and oil return process ends.

In summary, the embodiment of the present invention proposes a "triaxial compression test without jacket" method that reveals mechanical characteristics of near field surrounding rocks, and provides corresponding assorted test devices and test steps. It is also found that the device is also applicable to a triaxial test by gas confining pressure. In order to more clearly illustrate the technical solutions of the device 10, system and method for triaxial compression test with/without jacket by gas confining pressure on rock in accordance with the embodiment of the present invention, design ideas thereof are described below.

A basic test principle is to construct a separate space within the triaxial cell 20 and keep the high-pressure air in the space to be in direct contact with the core sample 100. In order to realize the direct contact between the rock core and the high pressure gas without changing the overall framework of a test machine, the triaxial cell 20 and the hydraulic system, it is planned to add a transparent cylinder within the triaxial cell 20, and the high pressure gas is injected into the cylinder, and the high pressure gas is kept in the cylinder.

For the purpose of convenient description, the transparent cylinder within the device 10 is referred to as a "small triaxial cell", and the triaxial cell 20 of the test machine itself is referred to as a "large triaxial cell". A through hole is disposed at the lower end of the side wall of the "small triaxial cell", which is capable of keeping a mutual communication with the "large triaxial cell", keeping a pressure balance. The high-pressure gas is applied on the core sample 100 within the "small triaxial cell" via the high pressure gas cylinder, and the high pressure gas acts directly on the exposed core. The through hole at the lower end of side wall of the "small triaxial cell" can transfer the pressure of the high-pressure gas within the "small triaxial cell" to the aviation hydraulic oil 500 within the "large triaxial cell". Finally the test machine's own "large triaxial cell" bears the pressure within the entire pressure chamber, and it does not need the "small triaxial cell" to bear the pressure because of a balance between an internal pressure and an external pressure.

In some embodiments, the "small triaxial cell" fulfills two functions: (1) within the large triaxial cell, a space is constructed with the small triaxial cell to keep the high-pressure air within the small triaxial cell and be in direct contact with the test sample; and (2) the core is within the transparent cylinder even if the core collapses and scatters, thus a test machine will not be contaminated or corroded.

The functions of the through hole below the small triaxial cell include: (1) the small triaxial cell is enabled to be in communication with the large triaxial cell to keep the pressure balance; and (2) a connection line of a sensor on a surface of the test sample is connected with a jack in the lower platen of the large triaxial cell through the through hole, and the number of the through holes can be designed according to needs, and 1-4 through holes are recommended.

In addition, with respect to the design of the small triaxial cell, the following points are mainly considered: (1) the through hole is disposed at the lower end of the side wall of the small triaxial cell for facilitating a wiring of the strain gauge and injecting oil from the bottom; and (2) a through hole is disposed on the small triaxial cell to serve as a gas inlet and outlet hole.

Based on the above design ideas, in a preferred embodiment, the device 10 for triaxial compression test with/without jacket by gas confining pressure on rock in accordance with the embodiment of the present invention includes a lower platen 104, a transparent resin cylindrical side wall 103, a cover plate 102 and two adsorption-type rubber annular suction cups. The connection relationship is as follows: the lower platen 104 is connected with one adsorption-type rubber annular suction cup in an adsorption manner, and the adsorption-type rubber annular suction cup is connected with a lower end of the cylindrical side wall 103; the third through hole 113 is disposed at the bottom of the cylindrical side wall 103; an upper end of the cylindrical side wall 103 is connected with another adsorption-type rubber annular suction cup, which is connected with the cover plate 102 in the adsorption manner; a first through hole 111 and a second through hole 112 are disposed on the cover plate 102, wherein the first through hole 111 is disposed in the center of the cover plate 102 and is for the upper end cap 141 disposed above the core sample 100 to pass through, and the cover plate 102 and the upper end cap 141 are sealed by a rubber ring 160 therebetween, the second through hole 112 is connected with the first rubber stopper with a hole 130, the first rubber stopper with a hole 130 is connected with a U-shaped tube, the U-shaped tube is connected with a rubber tube, the rubber tube is connected with the second rubber stopper with a hole 202 on the lower platen of the test machine's own triaxial cell 20, and the second rubber stopper with a hole 202 is connected with the gas inlet and outlet 201 disposed on the lower platen of the test machine's own triaxial cell 20. The core sample 100 with the upper end cap 141 and the lower end cap 142 is placed on a core tray 1042 on the lower platen 104 of the device 10, and is located by the locating pin 1043 on the core tray 1042 and the locating hole on the lower end cap 142.

An inner diameter of the device 10 for triaxial compression test with/without jacket by gas confining pressure on rock, that is, the inner diameter of the cylindrical side wall 103, is required to be capable of accommodating the core sample 100 and radial and circumferential sensors around the core sample. In addition, as the device 10 for triaxial compression test with/without jacket by gas confining pressure on rock needs to be installed in the triaxial cell 20 of the test machine during the test, an outer diameter of the device 10 is required to be less than the inner diameter of the test machine's own triaxial cell 20, moreover, the lower platen 104 of the device 10 does not cover the first oil port 231 or the gas inlet and outlet 201 in the lower platen of the test machine's own triaxial cell 20. A maximum height of the device 10 is less than the height of the inner wall of the test machine's own triaxial cell 20, and the upper end cap 141 above the core sample 100 is enabled to extend exactly out of the first through hole 111 on the cover plate 102 of the device 10, wherein the upper end cap 141 can move within a certain measuring range, and an axial displacement of the core sample 100 is within the range, so that the axial pressure loading end cap within the test machine's own triaxial cell 20 is unlikely to crush the device 10. When these conditions are satisfied, dimensions of various components of the device 10 can be respectively designed according to a size of the core sample 100 (the dimension of the core sample 100 includes Ø100×200 mm, Ø50×100 mm, and Ø78×150 mm).

At this time, the device 10 for triaxial compression test with/without jacket by gas confining pressure on rock in accordance with embodiments of the present invention has the following advantages: (1) simple structure: no complicated machining is required; (2) independent device: the dependency on the triaxial cell 20 and the hydraulic system of the test machine is not high, and the device 10 can be used with any type of triaxial test machines that can perform a test of gas permeability, and if a triaxial test machine cannot be used for performing a test of permeability, a lower platen of a triaxial cell 20 is modified, for example, a gas inlet and outlet passage, namely, the gas inlet and outlet 201 is added; (3) convenient assembly: the three main components can be assembled only by adsorption; (4) good observability: the main part of the device 10 is the transparent cylindrical side wall 103 at the middle, the condition within which can be seen; (5) a low requirement for sealing: because the device 10 and the triaxial cell 20 of the test machine are in communication with each other, the pressure is balanced, no precise sealing is required, and only ordinary seal is ok; and (6) the device 10 can be used to simulate the mechanical characteristics of the core sample 100 not only under the action of high pressure air, but also other gases, such as natural gas, nitrogen, and the like.

For example, a certain high temperature and high pressure test machine is modified to achieve a device 10 for triaxial compression test with/without jacket by gas confining pressure on rock. The high temperature and high pressure test machine has a pedestal on a lower platen of a triaxial cell 20, so the lower platen 104 designed for the device 10 can be omitted, and the adsorption-type rubber annular suction cup connected at the lower end of the cylindrical side wall 103 can be directly adsorbed to the lower platen of the triaxial cell 20 of the high temperature and high pressure test machine.

An inner radius of the triaxial cell 20 of the high temperature and high pressure test machine is 95 mm, the inner radius of the pedestal on the lower platen is 50 mm, and a distance from a first oil port 231 and a gas inlet and outlet 201 on the lower platen to the center of the lower platen is 70 mm.

Based on geometrical parameters of the triaxial cell 20 of the test machine, an inner diameter of the cylindrical side wall 103 of the device 10 can be designed to be 60 mm, the wall thickness is 2 mm, and the height is 250 mm. The size of the cover plate 102 is matched with the inner diameter of the cylindrical side wall 103, the thickness of the cover plate 102 is 5-10 mm, the inner diameter of a first through hole 111 in the center of the cover plate 102 is 50 mm, a diameter of a second through hole 112 on the cover plate 102 is 5-10 mm, and the diameter of a third through hole 113 of the bottom of the cylindrical side wall 103 is 5-10 mm. This design is applicable for a 50×100 mm cylindrical core sample 100. The height of the lower end cap 142 is 150 mm, and the diameter thereof is 50 mm. The annular gap between the inner wall of the cylindrical side wall 103 and the lower end cap 142 is 5 mm.

An assembly process of the device includes:

(1) assembling a sample

End caps and the sample are assembled from bottom to top, preferably, an upper end cap 141 is first nested in a first through hole 111 on the cover plate 102, thereby facilitating an installation in the next step, and then a strain gauge is installed on a core sample 100.

(2) Assembling a device 10 for triaxial compression test with/without jacket by gas confining pressure on rock.

An adsorption-type rubber annular suction cup connected at a lower end of the cylindrical side wall 103 is absorbed on the lower platen of the triaxial cell 20 of the test machine, and a wiring harness of the strain gauge installed on the core sample 100 is caused to pass through the third through hole 113 of the bottom of the cylindrical side wall 103.

A test implementation process includes:

(1) oil injection

The oil is injected into a space between the triaxial cell 20 of the test machine and the device 10 according to step S103 in the forgoing method for triaxial compression test with/without jacket by gas confining pressure on rock.

(2) Gas deflation and oil return

A part of hydraulic oil 500 within the triaxial cell 20 of the test machine is released into the device 10 according to the foregoing step S204, so that the gas does not leak from the third through hole 113 of the device 10 into the triaxial cell 20 of the test machine during the test. It should be noted that, an amount of gas deflation is required to enable a height of the hydraulic oil 500 entering into the device 10 to exceed the height of the second through hole 112 but not to exceed the height of the lower end cap 142, so as to avoid a contact between the hydraulic oil 500 and the core sample 100.

It is assumed that the height of the hydraulic oil 500 entering into the device 10 is less than or equal to 5 cm from the upper end of the lower end cap 142, then a maximum amount of gas deflation is:

annular cross section area of the annular gap=$\pi \times 3^2 - \pi \times 2.5^2 = 8.639$ cm$^2$;

If the height of the hydraulic oil 500 within the device 10 is 10 cm, volume of deflation=$8.639$ cm$^2 \times 10$ cm=$86.39$ ml.

(3) Application of a gas confining pressure

A high pressure gas cylinder is connected with the gas inlet and outlet 201 on the lower platen of the triaxial cell 20 of the test machine, a valve at the gas inlet and outlet 201 is opened to begin injecting the gas into the device 10 until a specified confining pressure is applied on the core sample 100 by the gas within the device 10. Since the device 10 is in communication with the triaxial cell 20 of the test machine, the pressure in the device 10 is the same as the pressure in the triaxial cell 20 of the test machine, the device 10 is not required to bear any pressure difference, and all the pressure is borne by the triaxial cell 20 of the test machine. It should be noted that a pressurization process of the gas cylinder can be achieved by manually opening and closing the valve, and can also be achieved through a computer servo control system.

(4) Start of the test and continuous loading of the axial pressure

An axial pressure loading process can refer to an existing triaxial test process. For example, at the beginning, the axial pressure is loaded with a force, and a loading rate is 2.5 kN/min, and the axial pressure is loaded to 20 kN at first, then an axial displacement control manner is used, and the loading rate is 0.2 mm/min, finally the test ends after the peak value is achieved.

(5) End of the test

After the test ends, a connection between the gas inlet and outlet 201 on the lower platen of the triaxial cell 20 of the test machine and the high pressure gas cylinder is disconnected, the gas port valve 222 disposed at the gas inlet and outlet 201 is opened to release the high pressure gas within the device 10. It should be noted that people cannot face to the gas inlet and outlet. When the pressure within the device 10 is released to 1-2 MPa, the gas port valve 222 can be closed, and then the first oil port 231 on the lower platen of the triaxial cell 20 of the test machine is opened, and the aviation hydraulic oil 500 is discharged by using the gas pressure remained within the device 10.

Then, the triaxial cell 20 of the test machine and the device 10 are opened in sequence, and the test ends.

Although the preferred embodiments of the present invention have been described, those skilled in the art can make additional changes and modifications to these embodiments once learning the basic inventive concepts. Therefore, the appended claims are intended to be interpreted as including the preferred embodiments and all the changes and modifications that fall within the scope of the present invention.

Apparently, those skilled in the art can make various modifications and variations to the present invention without departing from the spirit and scope of the present invention. Thus, if these modifications and variations of the present invention fall within the scope of the claims of the present invention and their equivalents, the present invention is also intended to include these modifications and variations.

What is claimed is:

1. A device for triaxial compression test with/without jacket by gas confining pressure on rock, applied for a system for triaxial compression test with/without jacket by gas confining pressure on rock, wherein the system further comprises a triaxial cell, and the device comprises a container, and wherein,
    an accommodating cavity is disposed within the container for placing a core sample;
    a first through hole and a second through hole are respectively disposed at an upper end of the container, the first through hole is for an end cap for loading an axial pressure on the core sample to penetrate through, and the second through hole is used for injecting gas into the accommodating cavity so as to apply a confining pressure on the core sample by the gas entering into the accommodating cavity;
    a third through hole is disposed at a lower end of a side wall of the container, and used for communicating the accommodating cavity with the triaxial cell; and
    a communicating tube, wherein one end of the communicating tube is in sealed fit with the second through hole and in communication with the accommodating cavity, and the other end of the communicating tube is used for connecting a gas inlet and outlet provided on the triaxial cell,
    wherein the communicating tube comprises a first connecting tube and a second connecting tube, and wherein one end of the first connecting tube is in sealed fit with the second through hole, the other end of the first connecting tube is connected with one end of the second connecting tube, and the other end of the second connecting tube is used for connecting the gas inlet and outlet provided on the triaxial cell.

2. The device according to claim 1, further comprising a first rubber stopper with a hole, wherein one end of the communicating tube is in sealed fit with the second through hole through the first rubber stopper with a hole.

3. A system for triaxial compression test with/without jacket by gas confining pressure on rock, comprising a triaxial cell and the device for triaxial compression test with/without jacket by gas confining pressure on rock according to claim 1, wherein the device is installed within the triaxial cell; and
    a gas inlet and outlet is provided on a lower platen of the triaxial cell, the gas inlet and outlet is used for connecting an external air inflation and pressurization device, and the gas inlet and outlet is in communication with the second through hole of the device through a communicating tube.

4. The system according to claim 3, wherein an outer end of the gas inlet and outlet is provided with an intake tube stretching out of the triaxial cell, and a gas port valve for controlling a connection and disconnection of the intake tube is provided on the intake tube.

5. The system according to claim 3, wherein an inner end of the gas inlet and outlet is provided with a second rubber stopper with a hole, and an outer wall of the second rubber stopper with a hole is in sealed fit with an inner wall of the gas inlet and outlet, a conduit in sealed fit with the hole of the second rubber stopper with a hole is disposed within the hole, and the communicating tube is in communication with the gas inlet and outlet through the conduit.

6. The system according to claim 3, further comprising an external liquid storage device and a liquid delivery tube, wherein the external liquid storage device is used for storing hydraulic oil, one end of the liquid delivery tube is in communication with a first oil port of the upper end of the triaxial cell, and the other end of the liquid delivery tube is immersed into the hydraulic oil within the external liquid storage device.

7. A method for triaxial compression test with/without jacket by gas confining pressure on rock, implemented on the basis of the device for triaxial compression test with/without jacket by gas confining pressure on rock according to claim 1, wherein the method comprises:
    mounting a core sample in the container of the device;
    mounting the device in the triaxial cell, and causing an end cap to pass through a first through hole of the device until contacting a top of a core sample, wherein the end cap is used for loading an axial pressure to the core sample;

injecting hydraulic oil into a space between the triaxial cell and the container through a first oil port of a lower platen of the triaxial cell;

connecting a gas inlet and outlet of the triaxial cell with an air inflation and pressurization device, inflating the container through the air inflation and pressurization device, the gas inlet and outlet, the communicating tube and a second through hole of the device so as to apply a confining pressure with a preset magnitude to the core sample;

loading the axial pressure to the core sample according to a preset rule;

releasing a high pressure gas within the device, and discharging the hydraulic oil within the triaxial cell, after the test ends.

8. The method according to claim 7, wherein a lower end cap is installed within the container of the device, the core sample is installed on the lower end cap, one end of the lower end cap is connected with a lower platen of the container, the other end of the lower end cap is connected with the bottom end of the core sample, and between the step of injecting hydraulic oil into the space between the triaxial cell and the container through the first oil port of the lower platen of the triaxial cell and the step of connecting the gas inlet and outlet of the triaxial cell with the air inflation and pressurization device, the method further comprises:

connecting a second oil port of the upper end of the triaxial cell to an external liquid storage device holding the hydraulic oil through a liquid delivery tube, so that the hydraulic oil within the external liquid storage device flows into the triaxial cell through the second oil port, and then into the container through a third through hole of the device; and wherein a height of the hydraulic oil flowing into the container exceeds the height of the third through hole in the device, but does not exceed the height of the lower end cap installed within the container.

* * * * *